(12) United States Patent
Marsh

(10) Patent No.: US 8,574,165 B2
(45) Date of Patent: Nov. 5, 2013

(54) HYDRATION MONITOR

(75) Inventor: Leon Thomas Lee Marsh, Shere (GB)

(73) Assignee: Inova Design Solutions Ltd, Guildford, Surrey (GB)

( * ) Notice: Subject to any disclaimer, the term of this patent is extended or adjusted under 35 U.S.C. 154(b) by 1064 days.

(21) Appl. No.: 10/598,334

(22) PCT Filed: Mar. 3, 2005

(86) PCT No.: PCT/GB2005/000816
§ 371 (c)(1),
(2), (4) Date: Aug. 24, 2006

(87) PCT Pub. No.: WO2005/084531
PCT Pub. Date: Sep. 15, 2005

(65) Prior Publication Data
US 2008/0234600 A1    Sep. 25, 2008

(30) Foreign Application Priority Data
Mar. 4, 2004    (GB) ................... 0404961.5

(51) Int. Cl.
*A61B 5/01*    (2006.01)
(52) U.S. Cl.
USPC ................ 600/549; 600/300; 600/547
(58) Field of Classification Search
USPC ........................ 600/307, 549, 547
See application file for complete search history.

(56) References Cited

U.S. PATENT DOCUMENTS

| | | | |
|---|---|---|---|
| 4,398,543 A * | 8/1983 | Sandlin et al. | 600/573 |
| 4,697,450 A * | 10/1987 | Bachman et al. | 73/23.2 |
| 5,089,477 A * | 2/1992 | Fregly et al. | 514/23 |
| 5,131,390 A * | 7/1992 | Sakaguchi et al. | 600/346 |
| 5,381,796 A * | 1/1995 | Pompei | 600/474 |
| 5,403,921 A * | 4/1995 | Montner et al. | 424/722 |
| 5,673,692 A | 10/1997 | Schulze et al. | |
| 5,907,091 A * | 5/1999 | Pause | 73/38 |
| 6,138,079 A | 10/2000 | Putman | |
| 6,287,255 B1 * | 9/2001 | Endo et al. | 600/307 |
| 6,439,028 B1 * | 8/2002 | Imhof | 73/29.01 |
| 6,524,239 B1 * | 2/2003 | Reed et al. | 600/300 |
| 6,540,686 B2 * | 4/2003 | Heikkila et al. | 600/483 |
| 6,746,398 B2 * | 6/2004 | Hervy et al. | 600/300 |
| 6,790,178 B1 * | 9/2004 | Mault et al. | 600/300 |

(Continued)

FOREIGN PATENT DOCUMENTS

| | | |
|---|---|---|
| EP | 1 177 763 A | 2/2002 |
| GB | 2 356 052 A | 5/2001 |
| GB | 2 357 576 A | 6/2001 |
| WO | WO 90/00366 A1 | 1/1990 |
| WO | WO 01/28416 A | 4/2001 |
| WO | WO 2005/015163 A3 | 2/2005 |

OTHER PUBLICATIONS

Michael J. Buono Anthony J. Wall, "Effect of hypohydration on core temperature during exercise in temperate and hot environments", Published online: Apr. 29, 2000, © Springer-Verlag 2000.*

(Continued)

*Primary Examiner* — Sean Dougherty
(74) *Attorney, Agent, or Firm* — Leason Ellis LLP

(57) ABSTRACT

A hydration monitor includes a temperature sensor (20; 65) for measuring a subject's core body temperature and a processor (30). The processor is arranged to accept measurements from the temperature sensor (20; 65) and calculate a hydration level in dependence on changes in the measured core body temperature.

16 Claims, 2 Drawing Sheets

(56) References Cited

U.S. PATENT DOCUMENTS

| | | | |
|---|---|---|---|
| 6,808,473 B2* | 10/2004 | Hisano et al. | 482/8 |
| 6,942,015 B1* | 9/2005 | Jenkins | 165/46 |
| 7,020,508 B2* | 3/2006 | Stivoric et al. | 600/390 |
| 7,133,716 B2* | 11/2006 | Kraemer et al. | 600/547 |
| 7,285,090 B2* | 10/2007 | Stivoric et al. | 600/300 |
| 7,306,565 B2* | 12/2007 | Fraden et al. | 600/549 |
| 7,344,508 B2* | 3/2008 | Surina | 600/587 |
| 7,402,135 B2* | 7/2008 | Leveque et al. | 600/306 |
| 7,493,232 B1* | 2/2009 | Surina | 702/160 |
| 7,783,344 B2* | 8/2010 | Lackey et al. | 600/547 |
| 2003/0092975 A1* | 5/2003 | Casscells et al. | 600/300 |
| 2004/0079517 A1* | 4/2004 | Bueley et al. | 165/46 |
| 2004/0167386 A1* | 8/2004 | Kasahara et al. | 600/382 |
| 2005/0070778 A1* | 3/2005 | Lackey et al. | 600/366 |
| 2006/0150714 A1* | 7/2006 | Imhof | 73/29.01 |
| 2008/0039700 A1* | 2/2008 | Drinan et al. | 600/301 |
| 2008/0125631 A1* | 5/2008 | Imhof | 600/307 |
| 2012/0092156 A1* | 4/2012 | Tran | 340/539.12 |
| 2012/0092157 A1* | 4/2012 | Tran | 340/539.12 |

OTHER PUBLICATIONS

ZA887082, Feb. 28, 1989, Telemetric Temperature Measurement, Jan Heunis et al.*

Yamazaki, F., et al., "A comparison of sweating responses during exercise and recovery in terms of sweating rate and body temperature," *International Journal of Biometeorology*, vol. 37, No. 4, pp. 212-217, Dec. 1993.

Montain, S. et al., *Influence of graded dehydration on hyperthermia and cardiovascular drift during exercise.* J. Appl. Physiol. 73(4): 1340-1350, 1992.

Sawka, M. et al., *Thermoregulatory and blood responses during exercise at graded hypohydration level.* J. Appl. Physiol. 59(5): 1394-1401, 1985.

Strydom, N.B. et al., *The effects of different levels of water deficit on physiological responses during heat stress.* Int. Z. angew. Physiol. einschl. Arbeitsphysiol. 26, 95-102, 1968.

* cited by examiner

HYDRATION MONITOR

FIELD OF THE INVENTION

The present invention relates to a hydration monitor and in particular to a portable hydration monitor suitable for use during exercise.

BACKGROUND TO THE INVENTION

In sport, particularly athletics, international competition is the ultimate challenge to the various regulatory systems of the body: physiological; biochemical; biomechanical and psychological. The body experiences a great challenge to accommodate the metabolic, thermal and other demands of intense exercise, where this challenge is greatest during endurance events in hot environments.

Since water serves the role of controlling most of the body's regulatory systems, the need for fluid intake during exercise is one of the main concerns, if not the primary concern, for the sportsperson in ensuring they can maintain their maximum sporting potential. The body's management of its hydration status is essential in its main roles of regulating body temperature; blood circulation, volume, viscosity and pressure; facilitating muscle movement and for removing waste.

A deficient level of hydration can lead to dehydration, a process referring to a loss of body water, from a state of hyperhydration (greater than normal body water content) to euhydration (normal body water content) or from euhydration downward to hypohydration (less than normal body water content).

In terms of performance, a subject who is just 2% dehydrated can see their performance drop by 20-30%, when compared to being in a state of euhydration. Put in context, this reduction in performance compares to the margin between winning gold and finishing outside of the medals, 7 seconds adrift, in the 1500 m in the 2000 Sydney Olympics.

It is important, however, to emphasise that hydration is not the only factor that should be monitored in exercise. Other factors such as energy stores, levels of electrolytes, fatigue, psychological factors and fitness (reduced fitness in elite athletes is due to insufficient recovery time to regain fitness after sustaining an injury) all have an effect on the performance of the sportsperson, and since the nature of sport is based around precision, an imbalance of any of these factors can lead to underachievement. In extreme cases, it has been known for a deficiency of electrolytes to be fatal, inducing a condition known as hyponatremia. The condition is often brought on through the dilution of sodium content in the blood, where the subject has consumed too much fluid without an adequate replacement of sodium.

It is the occasion where an athlete has the perfect balance of the above factors that they will perform at their lifetime best. A performance such as this requires the mind of the athlete to be in harmony with their body, an occurrence known simply as 'the zone'. It is an altered state of consciousness where the body and mind function automatically.

It is therefore desirable to be able to monitor hydration levels to achieve maximum possible performance. It is particularly desirable to be able to measure hydration levels during exercise to determine the quantity of liquid that should be taken on board to maintain, or reach, ideal hydration levels.

Current systems used for measuring hydration include osmometers and refractometers. Such systems are used by sporting bodies and clubs, although due to the size of the apparatus involved and the nature of the measurements taken, the systems can only be used before, during a stationary phase, or after an exercise is finished.

Osmometers work on the principle of either freezing point depression or vapour pressure (heating and cooling). Osmometers determine the number of water particles in a blood solution obtained from a subject by taking a blood sample. Another form of osmometry measures the concentration of water in a urine sample. In both cases, osmometry is not practical for use during exercise due to the need to collect blood or urine samples.

Refractometers measure the specific gravity of urine samples. By placing a drop of urine on the screen, the concentration of the urine is read off from a scale, the reading being determined by the refraction of light through the urine. The reading on the scale can then be converted into a number of milli-osmos per Kilogram.

Again, it is not practical for use during exercise due to the need of a urine sample. Although portable skin hydration monitors exist, such devices are designed for use in dermatology as a measure for skin moisture. Skin hydration monitors measure moisture levels in the corneocytes (dead skin cells) in the stratum corneum, the outer layers of the skin. In terms of body water, a normal moisture level in the stratum corneum could either be the result of, firstly, body euhydration or, secondly, sweating whilst in a dehydrated state. It therefore follows that skin hydration levels do not reflect body hydration. It is also not possible to determine the level and quantity of sweat, since the water in the stratum corneum reaches a maximum when the body is in a state of euhydration. Therefore it would not be possible to determine any excess sweat that evaporates or drips off the skin.

It has been suggested that blood flow monitors could be adapted to determine fluid status, through monitoring how peripheral blood flow varies during exercise to facilitate the dissipation of heat by the process of sweat and heat exchange. However, it is thought that this would not be a reliable method of monitoring hydration because sweat rates, and therefore blood flow rates, are greater in hot than in cold climates, even for the same level of dehydration. Peripheral blood flow fails to allow for other means of loosing fluid such as increased fluid exchange in cold climates between the environment and breath, where the environment draws moisture from the breath to try and equalize the two moisture levels.

It is understood from medical studies that for every 1% loss in body weight, due to dehydration, heart rates increase by about 7 beats per minute. From this, it may be possible to develop a heart rate monitor to calculate loss in hydration due to an increase in heart rate. However, it is not thought that such a monitor would be particularly accurate as heart rate increases could also be the result of other factors. For example, an increase in speed from one stride to the next would cause an increase in heart rate, as would anxiety, hormone levels, caffeine intake and the (varying) temperature of the atmosphere.

Bio-electrical Impedance Analysis (BIA) is another technique that has been suggested for use in measuring hydration. BIA analyses the amounts of fat, muscle and water in the body. The measure of hydration is separated into intracellular and extra cellular fluid compartments. BIA works by sending a small current through electrodes attached to the skin, normally on the hand and the foot. The current is sent at two different levels, one that can penetrate the cells of the body and one that cannot. The difference between the two provides an indication of the hydration status, on the theory that fluid facilitates the conduction of current. Currently, BIA results are affected by numerous variables including body position; hydration status; consumption of food and beverages; ambient air and skin temperature; recent physical activity; and the conductance of anything in contact with the skin, other than the electrodes. Thus, BIA lacks the precision and accuracy necessary for hydration monitoring, and it is doubtful that it could ever be adapted for use to determine fluid levels during even gentle exercise.

The present invention seeks to provide means for monitoring hydration in the body during exercise. It was therefore important to understand whether or not the theories behind any existing products could be developed for use in the PHM.

STATEMENT OF INVENTION

According to an aspect of the present invention, there is provided a hydration monitor comprising a temperature sensor for measuring a subject's core body temperature and a processor, the processor being arranged to accept measurements from the temperature sensor and calculate a hydration level in dependence on changes in the measured core body temperature.

In a preferred embodiment of the present invention, a portable monitor is arranged to measure core body temperature non-invasively. Hydration is monitored in real-time device and measurements are output via a display to the user. In this manner, a user can see his or her hydration status during exercise. Through this, it is intended that dehydration is avoided and thus performance maximised.

The portable hydration monitor is particularly useful as it can be used to analyse an athlete's performance to ensure their maximum sporting potential and it can be used to guarantee that the level of hydration is always safe. Thus, severe dehydration can be avoided, something that can ultimately be a risk to health and even survival.

Many internal and external variables (including psychological variables) are relative to the core body temperature that is measured. In particular, by use of a hydration monitor according to an embodiment of the present invention, stitch and stomach discomfort should be prevented.

Embodiments of the present invention could be used by almost all sportsmen/women including the disabled. Embodiments of the present invention could be produced specifically for impact sports. In particular, the earpiece or other temperature sensor would be designed so it could not be damaged by impact or be forced into the ear by jostling/impact.

Preferably, the temperature sensor includes one or more air flow channels allowing the flow of ambient air around the ear canal. Preferably, the temperature sensor is designed to stabily fit within the subject's ear and maintain a constant position. For example, the temperature sensor may be mounted within a malleable rubber member or similar to allow it to adaptably fit within different sized ears of subjects. In another alternative, various sized ear pieces may be provided to permit a subject to select the most appropriate fit.

In a preferred embodiment, the portable hydration monitor includes an earpiece containing a thermopile to measure core body temperature via the tympanic membrane (eardrum) and a wristwatch or other visual and/or audible indicator module that provides the user with real-time feedback and informs the user of how much fluid they must drink to re-hydrate their body to a level of euhydration (normal).

Preferably, the two units communicate wirelessly.

The thermopile detects incident infrared radiation from the tympanic membrane and provides a voltage equivalent to the core body temperature of the subject. This is then fed into an algorithm and the result is output via the indicator module.

Preferably, the result is the volume of fluid the subject should consume, in liters or ml to reach and/or maintain a level of euhydration.

Preferably, the monitor seeks to provide the athlete with a realistic accuracy of 0.5-1.0% BWL (body weight lost in water).

This present invention seeks to provide a portable hydration monitor suitable for monitoring hydration status throughout an exercise, which in turn would educate athletes during training so that the regular and appropriate intake of fluids is automatic, and in competition they can concentrate solely on performing in 'the zone' (they may not be wearing the device during competition).

Various embodiments may eventually be produced to cater for the various needs of:
- athletes (and novice sports person);
- military personnel;
- hospital patients and
- normal public users The hydration monitor may comprise an earpiece and a remote unit, the temperature sensor being positioned in the earpiece for measuring the core body temperature via the subject's tympanic membrane.

Preferably, the temperature sensor comprises a thermopile.

The earpiece may further comprises a transmitter, the remote unit including the processor, output means and a receiver, the earpiece being arranged to communicate measurements to the processor via the transmitter and receiver, the processor being arranged to provide an indication of the hydration level via the output means.

The transmitter and receiver may communicate wirelessly.

The transmitter and receiver may be transcievers.

The remote unit may comprise a selected one of:
- a wristwatch, a personal digital organizer, a mobile telephone, a personal computer or medical diagnostic and/or monitoring apparatus.

The output means may include one or more of a display and a speaker.

The monitor may further comprise a memory for storing hydration level and/or core body temperature over time.

The processor may be arranged to determine a hydration level by the following formula:

$$[(\text{core body temperature current} - \text{core body temperature normal}) \times \text{subject's weight}]/(\text{factor of ambient compensation} \times 100).$$

The factor of ambient compensation may be between 0.1 and 0.23 and is determined in dependence on the temperature of the environment surrounding the subject.

The hydration monitor may be arranged to operate repeatedly at predetermined time intervals.

The processor may be arranged to generate an alarm upon determination of a hydration level below a predetermined level.

According to another aspect of the present invention, there is provided a method of measuring hydration of a subject comprising the steps of:
- measuring an initial core body temperature of the subject;
- measuring a subsequent current core body temperature of the subject;
- subtracting the initial core body temperature from the subsequent core body temperature;
- multiplying by the subject's weight; and,
- dividing by a factor of ambient compensation.

Preferably, the measurements are taken from the subject's tympanic membrane.

BRIEF DESCRIPTION OF THE DRAWINGS

Embodiments of the present invention will now be described in detail, by way of example only with reference to the accompanying Figures, in which.

DETAILED DESCRIPTION

Figure 1:
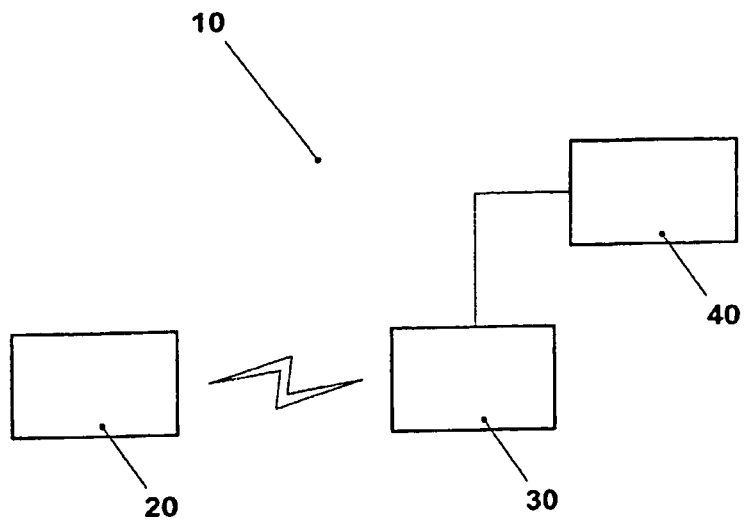
FIG. 1 is a block diagram of a hydration monitoring system according to an embodiment of the present invention.

FIG. 1 is a block diagram of a hydration monitoring system according to an embodiment of the present invention.

The hydration monitoring system 10 includes a temperature sensor 20, a processor 30 and a display 40.

The temperature sensor 20 is arranged to measure body temperature of a subject and communicate the measured temperature to the processor 30. Upon receipt of the measurement, the processor is arranged to calculate a body water level for the subject and output a corresponding hydration indication to the display 40.

Preferably, the temperature sensor 20 is arranged to measure temperature of a tympanic membrane within one of the subject's ears.

The calculation performed by the processor is carried out at regular intervals as follows:

$$[(\text{core body temperature current} - \text{core body temperature normal}) \times \text{weight}]/(\text{factor of ambient compensation} \times 100)$$

The normal core body temperature will have been determined and/or input into the device prior to use. The normal core body temperature is subtracted from the current core body temperature, multiplied by the weight of the subject in kg, (although could also be configured to accept pounds depending on user's preference) and then divided by the factor of ambient compensation. This is then either divided by one hundred to give a measurement in liters or alternatively multiplied by ten to give the measurement in milliliters.

The factor of ambient compensation is valued between 0.1 and 0.23 degrees centigrade, and refers to the increase in the subject's core body temperature for every percent loss of body weight, in temperate and hot climates respectively.

The measurement is the amount of liquid that the subject should drink to achieve euhydration (full hydration).

Figure 2:
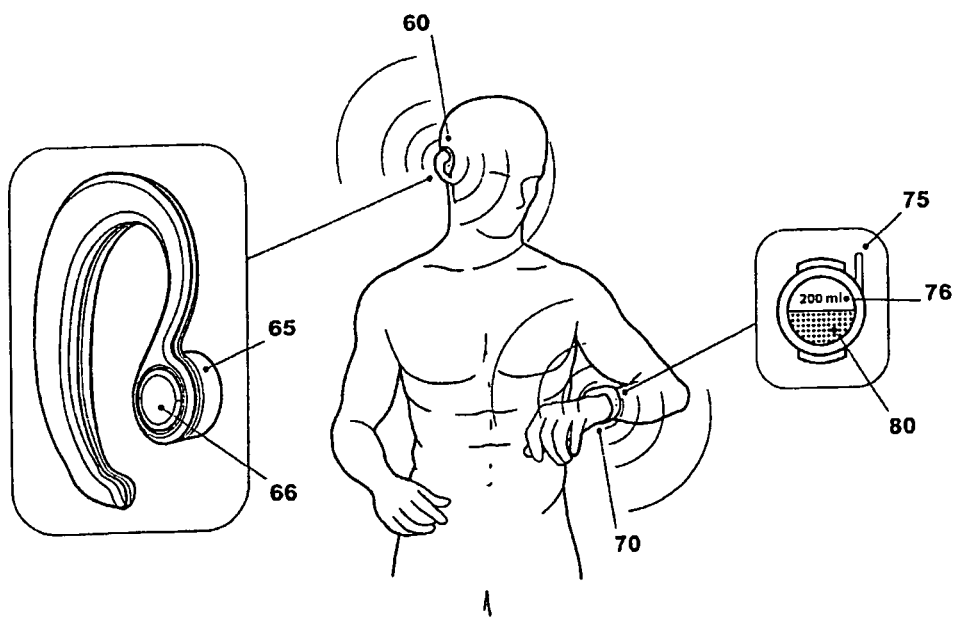
FIG. 2 is a schematic diagram of a portable hydration monitor incorporating the system of FIG. 1.
Figure 3:
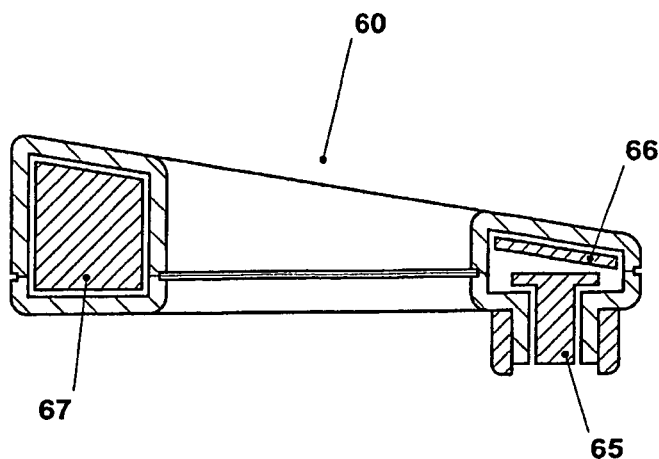
FIG. 3 is a cross-sectional diagram of an earpiece of the monitor of FIG. 2; and, FIG. 4 is a schematic diagram of another system according to an embodiment of the present invention.

FIG. 2 is a schematic diagram of a portable hydration monitor incorporating the system of FIG. 1. FIG. 3 is a cross-sectional diagram of an earpiece of the monitor of FIG. 2.

The portable hydration monitor includes an earpiece 60 and a wristwatch 70.

The earpiece 60 includes a thermopile 65 positioned to measure core body temperature via the tympanic membrane when inserted into an ear of a subject and a transmitter 66 arranged to communicate temperature measurements to the wristwatch 70.

The transmitter and receiver could be transceivers to allow the two units to talk to each other for initialization etc.

The wristwatch 70 includes a receiver 75 arranged to receive measurements from the earpiece, a processor to perform the calculations discussed above and a display 76 to provide the subject with feedback on their hydration status.

Preferably, the display also informs the user of how much fluid they must drink to re-hydrate their body to a level of euhydration (normal). Preferably, the monitor operates on a substantially real-time basis.

In addition or as an alternative to the display 76, the wristwatch 70 may include an audible indicator 80 to provide the feedback and/or additional alerts. For example, hydration status and feedback may be provided via the display 76 and alerts may be provided via the audible indicator 80 when a predetermined level of dehydration is reached and/or immediate action is necessary.

Preferably, the transmitter 66 and receiver 75 communicate via a wireless data protocol such as BlueTooth™ or another suitable wireless communication system. The earpiece 60 and wristwatch 70 both include one or more batteries to supply power. At least in the case of the earpiece 60, it is preferred that the battery 67 is rechargeable from within the earpiece via a suitable connection to a power-source or inductive coupling to a power-source. In order to conserve battery power, the transmitter 66 may establish a connection with the receiver only when it is provided with data to transmit. The earpiece 60 and/or wristwatch may include a sleep mode to further conserve power when not in use.

When inserted into a subject's ear canal, the thermopile 65 detects incident infrared radiation from the tympanic membrane and provides a voltage equivalent to the core body temperature of the subject. This is transmitted to the wristwatch and used by the processor to obtain a hydration indication for output via the display and/or audible indicator. Preferably, the result is the volume of fluid the subject should consume, in liters or ml.

Preferably, the wristwatch includes a memory and is connectable to a computer or other remote station, either via a wireless connection or via a docking station or other wired connection to enable the subject to store and subsequently download core body temperature and/or hydration statistics and other relevant information for subsequent analysis.

If configured by the user, an alert can be set to sound periodically (for example, every minute) to indicate when the temperature is measured. The alert will preferably be generated in the earpiece but it could alternatively be generated from the wristwatch, or both. The alert is intended to remind the subject to look at the display and could also serve to indicate when the display is being updated. If ignored, and the subject becomes dehydrated, the device will sound an alarm, either in the earpiece or wristwatch or both when their hydration status falls below 2% of their level of euhydration.

Depending on the configuration of the wristwatch and earpiece, the user may be given a choice of a sound or vibration alert, or both.

It is understood from medical studies that for every 1% loss in body weight, due to dehydration, heart rates increase by about 7 beats per minute. From this, it may be possible to incorporate a heart monitor into embodiments of the present invention to provide more detailed information on hydration status. The heart rate monitor would be one of the many types currently available and would be arranged to communicate its measurements with the wristwatch in the same manner as the earpiece.

In addition, pressure detecting inserts could be included in an embodiment of the present invention. Such inserts would be inserted into shoes and arranged to measure weight by the pressure applied. This information could then be communicated to the wristwatch which could calculate a weight change due to fluid loss. This method is expected to be unreliable by itself as it is affected by balance distribution over the foot, for example running up or down slopes and speed changes. However, when used in combination with the temperature measurements from the earpiece and possibly the heart rate measurements from the heart rate monitor, accuracy could quite possibly be increased. As an alternative to inserts, a pressure sensor could be integrated into a treadmill or other weight measurement mechanisms could be used.

Figure 4:
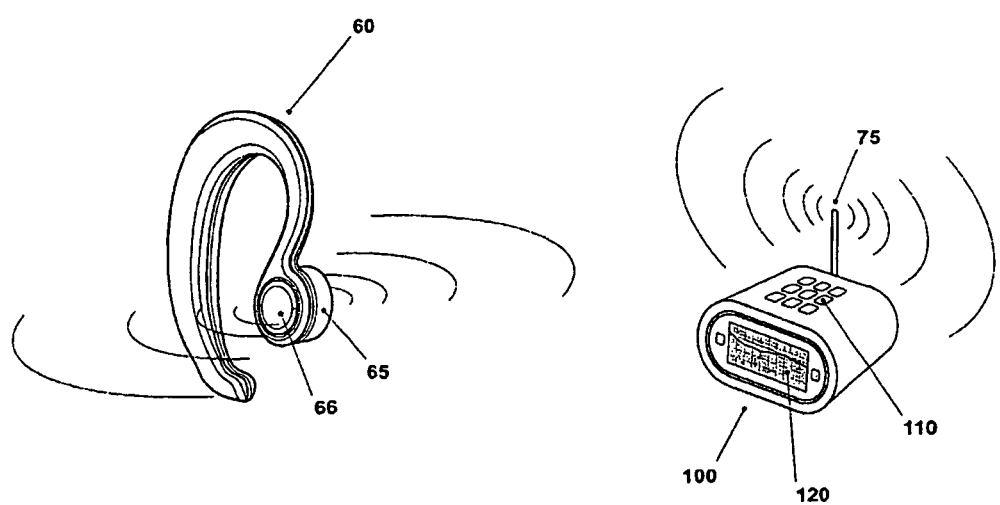

Various embodiments may eventually be produced to cater for the various needs of:
- athletes (and novice sportsperson);
- military. personnel;
- hospital patients and
- normal public users For example, whilst athletes may be interested in actual numeric levels, the public users may prefer an indicator in the form of a traffic light or similar (for example, green=hydration normal, amber=a little dehydrated, red=very dehydrated). Similarly, hospital patients themselves may not care about hydration levels—the output data could be passed to medical staff for analysis and determination of treatment or it may be fed into a control system for a fluid drip so that the fluid intake for a patient could be automatically adjusted. Some embodiments may include a memory and connection/transmission system so that data can be recorded over time and uploaded onto a computer for more detailed analysis of performance. An example embodiment of the present invention that may be used by medical personnel or trainers of sportsmen is shown in FIG. 4 in which the wristwatch is replaced by a base station 100. As the base station need not be portable, it can include a larger display 120 and/or more powerful speaker 110 and a receiver having a greater reception radius to allow the subject to move further from it and still be in contact. The base station could be used as well as a wristwatch so both the sportsman and the trainer is able to see hydration levels—indeed, they may even be provided different types of information depending on their needs.

The device could also, be used to prevent athletes reaching their 'ceiling temperature' and having to stop running in, for example, an ultra endurance event where the athlete is performing at their peak for several hours. An indication of extreme temperature would allow the athlete to reduce their speed and continue running instead of having to walk to cool down. This would apply even if there was no water available. Therefore by using the device they don't lose valuable time, and reduce the risk of damaging their body.

The device could also be used to determine cardiac changes in the body, particularly central blood volume, heart rate, stroke volume (these are relative to body water). This will help to prevent a reduction in cardiac output which will reduce the athletes performance, as described below:

In a preferred embodiment, the calculation used to determine hydration status may take account of fat percentage of body weight. This will address discrepancies in use where a subject has a large percentage of fat for body weight. Since fat contains little or no water, the device may not give accurate results for someone with a large percentage of fat content, as for that of a slender person (the slender person will no doubt have a greater percentage of water in their body than the fatter person).

Other factors that may be taken into account during the calculation may include the temperature of the surrounding environment. The magnitude of core temperature elevation can range from 0.1 to 0.23° C. for every percent of body weight lost, and is greater during exercise in hot, as opposed to temperate climates.

The invention claimed is:

1. A hydration monitor comprising a temperature sensor for measuring a subject's core body temperature and a processor, the processor being arranged to accept measurements from the temperature sensor and calculate a hydration level in dependence on changes in the measured core body temperature by the following formula:

[(core body temperature current−core body temperature normal)×subject's weight]/(a value between 0.10° C. and 0.23° C.×100).

2. A hydration monitor as claimed in claim 1, comprising an earpiece worn on the ear and a remote unit, the temperature sensor being positioned in the earpiece for measuring the core body temperature via the subject's tympanic membrane.

3. A hydration monitor as claimed in claim 2, wherein the temperature sensor comprises a thermopile.

4. A hydration monitor as claimed in claim 2, wherein the earpiece further comprises a transmitter, the remote unit including the processor, output means and a receiver, the earpiece being arranged to communicate measurements to the processor via the transmitter and receiver, the processor being arranged to provide an indication of the hydration level via the output means.

5. A hydration monitor as claimed in claim 4, wherein the transmitter and receiver communicate wirelessly.

6. A hydration monitor as claimed in claim 4, wherein the transmitter and receiver are transceivers.

7. A hydration monitor as claimed in claim 4, wherein the remote unit comprises at least one of: a wristwatch, a personal digital organizer, a mobile telephone, a personal computer or a medical diagnostic and a monitoring apparatus.

8. A hydration monitor as claimed in claim 4, wherein the output means includes one or more of a display and a speaker.

9. A hydration monitor as claimed in claim 1, further comprising a memory for storing at least one of the hydration level and the core body temperature over time.

10. A hydration monitor as claimed in claim 1 arranged to operate repeatedly at predetermined time intervals.

11. A hydration monitor as claimed in claim 1, wherein the processor is arranged to generate an alarm upon determination of a hydration level below a predetermined level.

12. A method of measuring hydration of a subject wherein the following steps are performed with a hydration monitor having a processor:
   a. measuring an initial core body temperature of the subject;
   b. measuring a subsequent current core body temperature of the subject;
   c. subtracting the initial core body temperature from the subsequent core body temperature, thereby obtaining a difference;
   d. multiplying the difference by the subject's weight using the processor, thereby obtaining a multiplied difference;
   e. dividing the multiplied difference by a value between 0.10° C. and 0.23° C., thereby obtaining an indication of the subject's hydration level;
   f. providing output indicative of the subject's hydration level from the hydration monitor to the subject.

13. A method as claimed in claim 12, wherein the measurements are taken from the subject's tympanic membrane.

14. A portable hydration monitor including:
   a. a wearable temperature sensor having:
      (1) an earpiece worn on the ear for measuring a subject's core body temperature via the subject's tympanic membrane, and (2) a transmitter configured to communicate said measured core body temperature; and b. a remote unit to be carried or worn by the subject and including a receiver, a processor, and an output device wherein:

(1) the receiver is configured to receive the communicated core body temperature from the transmitter and communicate the received core body temperature to the processor, (2) the processor is configured to:

i. calculate the subject's hydration level from the measured core body temperature in substantially real time, and ii. cause an indication of the hydration level to be output via the output device.

15. The portable hydration monitor of claim 14, wherein the earpiece includes one or more channels to allow ambient air to flow around the subject's ear canal.

16. The portable hydration monitor of claim 14, wherein the earpiece includes a sound generator, the portable hydration monitor being arranged to cause the sound generator to sound an alarm when the calculated hydration level is below a predetermined threshold.

\* \* \* \* \*